(12) United States Patent
Boe et al.

(10) Patent No.: US 9,322,747 B2
(45) Date of Patent: Apr. 26, 2016

(54) ISOTHERMAL SUBSEA SAMPLING SYSTEM AND METHOD

(75) Inventors: Asmund Boe, Paris (FR); Jonathan W. Brown, Aberdeen (GB); Paul B. Guieze, Fontenailles (FR); John A. Kerr, St Nom la Breteche (FR); Ricardo Vasques, Bailly (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 876 days.

(21) Appl. No.: 13/256,632

(22) PCT Filed: Mar. 16, 2010

(86) PCT No.: PCT/IB2010/051140
§ 371 (c)(1),
(2), (4) Date: Nov. 29, 2012

(87) PCT Pub. No.: WO2010/106500
PCT Pub. Date: Sep. 23, 2010

(65) Prior Publication Data
US 2013/0213149 A1    Aug. 22, 2013

Related U.S. Application Data

(60) Provisional application No. 61/160,446, filed on Mar. 16, 2009, provisional application No. 61/166,998, filed on Apr. 6, 2009, provisional application No. 61/232,487, filed on Aug. 10, 2009, provisional application No. 61/285,323, filed on Dec. 10, 2009.

(51) Int. Cl.
*G01N 1/02* (2006.01)
*E21B 49/00* (2006.01)
(Continued)

(52) U.S. Cl.
CPC .............. *G01N 1/02* (2013.01); *E21B 41/0007* (2013.01); *E21B 49/001* (2013.01); *E21B 49/08* (2013.01); *G01N 1/2035* (2013.01); *G01N 33/28* (2013.01); *G01N 2035/0489* (2013.01)

(58) Field of Classification Search
CPC ........ G01N 1/02; G01N 1/2035; E21B 49/08; E21B 49/001
See application file for complete search history.

(56) References Cited

U.S. PATENT DOCUMENTS

| | | | |
|---|---|---|---|
| 4,442,720 A | * | 4/1984 | Apley ................. G01N 1/2035 73/863.31 |
| 5,661,237 A | | 8/1997 | Dussan et al. |

(Continued)

FOREIGN PATENT DOCUMENTS

| | | |
|---|---|---|
| GB | 2406386 | 3/2005 |
| GB | 2447908 | 10/2008 |

(Continued)

OTHER PUBLICATIONS

"Improved Production Sampling Using the Framo Multiphase Flow Meter", Framo Engineering AS, 1999.

*Primary Examiner* — Paul West
(74) *Attorney, Agent, or Firm* — Conley Rose, P.C.

(57) ABSTRACT

A system and method for collecting a selected phase of a representative sample from a multiphase fluid flowing through a flowline, preferably located subsea. The system includes a multiphase sampling apparatus attachable to the flowline for sampling the representative sample; a vehicle sampling apparatus (e.g., ROV) locatable proximate the flowline having a power supply and a fluid sample collector for storing at least one selected phase of the representative sample; an interface for connecting the multiphase sampling apparatus and the vehicle sampling apparatus; and a temperature control arrangement disposed between the multiphase sampling apparatus and the vehicle sampling apparatus configured to minimize the temperature difference between the representative sample and the multiphase fluid flowing through the flowline.

43 Claims, 7 Drawing Sheets

(51) Int. Cl.
*E21B 41/00* (2006.01)
*E21B 49/08* (2006.01)
*G01N 1/20* (2006.01)
G01N 33/28 (2006.01)
G01N 35/04 (2006.01)

(56) References Cited

U.S. PATENT DOCUMENTS 6,435,279 B1    8/2002    Howe et al.

2004/0262008 A1    12/2004    Deans et al.
2007/0143023 A1    6/2007    Betancourt et al.
2007/0274842 A1    11/2007    Campen et al.
2010/0132449 A1*    6/2010    Birkett et al. ............... 73/152.27

FOREIGN PATENT DOCUMENTS

WO    2006/037565    4/2006
WO    2008/087156    7/2008

\* cited by examiner

ISOTHERMAL SUBSEA SAMPLING SYSTEM AND METHOD

CROSS REFERENCE TO RELATED APPLICATIONS

The present disclosure is based on and claims the benefit of priority from U.S. Provisional Patent Application Ser. No. 61/160,446 of Brown et al, entitled "SUBSEA SAMPLING SYSTEM AND METHOD," filed on Mar. 16, 2009; U.S. Provisional Patent Application Ser. No. 61/166,998 of Brown et al, entitled "SUBSEA SAMPLING SYSTEM AND METHOD," filed on Apr. 6, 2009; U.S. Provisional Patent Application Ser. No. 61/232,487 of Brown et al., entitled "ISOTHERMAL SUBSEA SAMPLING SYSTEM AND METHOD," filed on Aug. 10, 2009; and U.S. Provisional Patent Application Ser. No. 61/285,323 of Theron et al, entitled "SUBSEA SAMPLING SYSTEM AND METHOD," filed on Dec. 10, 2009; the entire contents of the disclosures of which are hereby incorporated by reference.

TECHNICAL FIELD

The present disclosure relates generally to sampling fluids in the oil and gas industry. More particularly, the present disclosure relates to an apparatus, system and method for sampling fluids subsea at line conditions.

DISCUSSION OF THE BACKGROUND

In the oil and gas industry, fluid samples are collected for analysis in many well applications. For example, in a subsea environment, tubing is used to convey well fluid to a desired location. Measurements and samples of the fluid moving through the tubing can provide useful information for improved operation of the well.

Fluid samples, for example, may be collected for reservoir characterization or to deduce reservoir fluid properties. The analysis generally is done at a land-based or field-deployed pressure/volume/temperature (PVT) laboratory. The information derived is used for periodic reservoir characterization over the life of a well to facilitate the evaluation of reserves, and for production planning and optimization.

Fluid samples are also collected to enable deposition studies, for example, samples may be collected to carry out asphaltene deposition studies. In subsea applications, problematic deposition of such materials can occur as a result of the temperature and pressure gradients between a subsea wellhead and the surface.

In many of these same well applications, PVT data and hydrogen sulphide ($H_2S$) level data are used to facilitate optimization of a well fluid production.

The PVT data, for example, can be used to correct volumetric correlations applied to flow meters, pipelines and other downstream assets. However, the detection of the various well parameters and the taking of samples for further analysis can be difficult and/or inefficient, particularly in certain environments, such as subsea environments.

Subsea sampling can be applied to single-phase or multiphase fluids. When the fluid is multiphase, the phases can be collected separately and analyzed independently. This information can be used to reduce the uncertainty of the results obtained by using multiphase flow meters.

Various apparatus, methods and systems for sampling and analyzing well fluids have been identified previously, including those used subsea. U.S. Pat. No. 6,435,279 discloses a method and apparatus for sampling fluids from an undersea wellbore utilizing a self-propelled underwater vehicle, and a collection and storage device.

International patent application PCT/EP2008/050445, published as WO 2008/087156, discloses a system and method for analysis of fluid samples. An article entitled "Improved Production Sampling Using the Framo Multiphase Flow Meter" by Framo Engineering AS (October 1999) discusses a multiphase flow meter used in fluid sampling including subsea with the aid of remotely operated vehicles (ROV).

Other technologies, such as Schlumberger's MDT sampling and analysis technologies also have been used for subsea sampling and analysis of fluids in the oil and gas industry. A further well known system used by Schlumberger for sampling fluids in the oil and gas industry is discussed in international patent application PCT/EP2005/010580, published as WO 2006/037565, the disclosure of which is hereby incorporated by reference.

SUMMARY OF THE INVENTION

In view of disadvantages inherent in the known types of solutions present in the prior art, exemplary implementations of the present disclosure are directed to novel methods and systems for sampling fluids subsea at line conditions.

According to an aspect of the present disclosure, a system for collecting at least one selected phase of a representative sample from a multiphase fluid flowing through a flowline is provided, the system including a multiphase sampling apparatus attachable to a flowline for sampling a representative sample of a multiphase fluid flowing through the flowline; a vehicle sampling apparatus locatable proximate the flowline, the vehicle sampling apparatus including a power supply and a fluid sample collector for storing the at least one selected phase of the representative sample; an interface for connecting the multiphase sampling apparatus and the vehicle sampling apparatus; and a temperature control arrangement disposed between the multiphase sampling apparatus and the vehicle sampling apparatus that minimizes the temperature difference between the representative sample and the multiphase fluid flowing through the flowline, the temperature control arrangement configured to receive power from the vehicle sampling apparatus.

The system is preferably locatable subsea. In this form of the present disclosure, the vehicle sampling apparatus is preferably a subsea remotely operated vehicle (ROV). As such, the ROV is preferably operable to transport the at least one selected phase of the representative sample remote from the flowline.

In an exemplary embodiment, the system further includes an enrichment arrangement in fluid communication with the fluid sample collector, the enrichment arrangement may be configured to detect at least one selected phase of the representative sample, and discard at least one other phase of the representative sample into the flowline. The enrichment arrangement may include a phase separator for separating the phases of the representative sample of the multiphase fluid. As such, the enrichment arrangement may be in fluid communication with a fluid pump or piston for discarding the at least one other phase of the representative sample into the flowline. The enrichment arrangement may be locatable entirely on the vehicle sampling apparatus, entirely on the multiphase sampling apparatus, entirely on the flowline, entirely on the interface, or proportionally distributed among each component of the system.

In another exemplary embodiment, the system further includes a pressure control arrangement having at least one fluid pump in fluid communication with at least one fluid connection point between the multiphase sampling apparatus and the vehicle sampling apparatus, wherein the at least one fluid pump is capable of minimizing the pressure difference between the representative sample and the multiphase fluid flowing through the flowline. Operable in combination with the at least one fluid pump, the system may further include at least one pressure sensor for measuring the pressure of the flowline acted upon by the multiphase fluid flowing through the flowline, and at least one other pressure sensor for measuring the pressure of the representative sample. Alternatively, however, the pressure control arrangement may include only one pressure sensor for measuring the pressure of the entire system.

In yet another exemplary embodiment of the present disclosure, the multiphase sampling apparatus may include a liquid-rich sampling port and a gas-rich sampling port in selective fluid communication with the multiphase fluid flowing through the flowline. The multiphase sampling apparatus may be permanently positioned on the flowline, or may be locatable on the vehicle sampling apparatus. The multiphase sampling apparatus may further include a flow conditioner positioned upstream of the liquid-rich sampling port and gas-rich sampling port relative to the direction of multiphase fluid flowing through the flowline. The flow conditioner may include an elbow portion in the flowline, or a flow conditioner as disclosed in co-pending U.K. Patent Application Nos. 2406386A and 2447908A, the disclosures of which are hereby incorporated by reference.

In an alternative exemplary embodiment of the present disclosure, the multiphase sampling apparatus may include a sampling probe capable of insertion into the flowline for sampling the representative sample of the multiphase fluid flowing through the flowline. The sampling probe may be permanently positioned on the flowline, or may be locatable on the vehicle sampling apparatus. The sampling probe may be insertable into and retractable from the flowline by an extension mechanism, such as a hydraulically operable piston. The sampling probe may further include at least one fluid analysis sensor. The sampling probe includes at least one inlet port for sampling the representative sample of the multiphase fluid. Preferably, the sampling probe includes a liquid-rich sampling port positioned near a superior portion of the flowline, and a gas-rich sampling port positioned near an inferior portion of the flowline.

In another aspect of the present disclosure, the system may include a fluid analysis sensor locatable on the vehicle sampling apparatus for analysis of the collected fluid sample. The fluid analysis may be performed either subsea or at surface. Such fluid analysis sensor may include, but is not limited to, sensors for measuring the nuclear attenuation of a gamma ray source one phase at a time performed at line conditions.

In an alternative aspect of the present disclosure, the system may include at least one fluid pump in fluid communication with the sampling apparatus, wherein the fluid pump is capable of cleaning the sampling apparatus sample lines. The fluid pump may be permanently positioned subsea, or may be locatable on the vehicle sampling apparatus.

In an exemplary embodiment of the present disclosure, the temperature control arrangement includes heating elements disposed upon a plurality of sample lines leading away from the multiphase sampling apparatus. The temperature control arrangement may further include at least one temperature sensor for measuring the temperature of the multiphase fluid flowing through the flowline, and at least one other temperature sensor for measuring the temperature of the representative sample. Alternatively, however, the temperature control arrangement may include only one temperature sensor for measuring the temperature of the entire system.

In another exemplary aspect of the present disclosure, the interface includes at least one fluid control valve operable by the vehicle sampling apparatus, a liquid-rich fluid connection point and a gas-rich fluid connection point for selectively transferring the at least one selected phase of the representative sample between the multiphase sampling apparatus and the vehicle sampling apparatus. The interface may further include at least one power connection point for transferring power to the temperature control arrangement, and at least one hydraulic connection point for actuating the multiphase sampling apparatus.

Another aspect of the present disclosure provides a method for collecting at least one selected phase of a representative sample from a multiphase fluid flowing through a flowline located subsea. The method including the steps of connecting a vehicle sampling apparatus having a power supply and a fluid sample collector to an interface located proximate a multiphase sampling apparatus, wherein the multiphase sampling apparatus is attachable to the flowline; measuring a pressure and temperature of the multiphase fluid flowing through the flowline; activating a temperature control arrangement and a pressure control arrangement to simulate conditions similar to the measured temperature and pressure of the multiphase fluid flowing through the flowline; selectively sampling the at least one selected phase of a representative sample from the multiphase fluid flowing through the flowline; and storing the at least one selected phase of the representative sample in the fluid sample collector at conditions similar to the measured temperature and pressure of the multiphase fluid flowing through the flowline.

In an exemplary aspect of the present disclosure, the method includes the step of enriching the at least one selected phase of the representative sample, wherein enriching includes: detecting the at least one selected phase of the representative sample; and discarding the at least one other phase of the representative sample into the flowline. In this aspect of the present disclosure, the method may further include separating the at least one selected phase of the representative sample from the at least one other phase of the representative sample.

According to an aspect of the present disclosure, the method further includes disconnecting the vehicle sampling apparatus from the interface. Moreover, the method further includes transporting the at least one selected phase of the representative sample stored in the fluid sample collector to a position remote from the flowline.

In an alternative aspect of the present disclosure, the method may include analyzing a plurality of fluid characteristics of the at least one selected phase of the representative sample. Such fluid analysis may be performed subsea or at surface.

In yet another aspect of the present disclosure, the method may further include cleaning the multiphase sampling apparatus by means of a fluid pump. In addition, the method may include pressure testing the multiphase sampling apparatus by means of a fluid pump locatable on the vehicle sampling apparatus.

In another exemplary embodiment of the present disclosure, the method may include inserting a sampling probe into the flowline and retracting the sampling probe from the flowline by an extension mechanism.

Advantageously, the present system and method for sampling and analysis of fluids in a flowline may be implemented in the subsea environment while keeping the sample fluid at line conditions. A further advantage is that the current system and method may be implemented without damaging or restricting the flow through the flowline. Another advantage is the representativeness of the sampling process, in other words, the sample phases can be selected and adequate quantities from these sample phases can be captured through an enrichment process.

Even further, the system and method can be adjusted subsea and thus used for a very wide range of fluids encountered subsea, from lean gas to heavy oil. The ability for the system to be adjusted is enhanced by, for example, the use of selected sensors which are deployed with the system, and which allow for the selective sampling of fluids of interest; as well as the use of an ROV, which can be modified in accordance with the fluid properties and subsea conditions.

An exemplary system and method of the present disclosure also allows for convenient cleaning and unblocking of the sample fluid flowlines and sampling apparatus.

These together with other aspects, features, and advantages of the present disclosure, along with the various features of novelty, which characterize the disclosure, are pointed out with particularity in the claims annexed to and forming a part of this disclosure. The above aspects and advantages are neither exhaustive nor individually or jointly critical to the spirit or practice of the disclosure. Other aspects, features, and advantages of the present disclosure will become readily apparent to those skilled in the art from the following description of exemplary embodiments in combination with the accompanying drawings. Accordingly, the drawings and description are to be regarded as illustrative in nature, and not restrictive.

BRIEF DESCRIPTION OF THE DRAWINGS

The disclosure will be better understood and aspects other than those set forth above will become apparent when consideration is given to the following detailed description thereof. Such description of the present disclosure is illustrated by way of example, and not by way of limitation, to the annexed pictorial illustrations, graphs, drawings, and appendices, in which like reference numerals refer to similar elements, and in which.

DETAILED DESCRIPTION

Specific embodiments of the present disclosure will now be described in detail with reference to the accompanying drawings. Further, in the following detailed description of embodiments of the present disclosure, numerous specific details are set forth in order to provide a more thorough understanding of the disclosure. However, it will be apparent to one of ordinary skill in the art that the embodiments disclosed herein may be practiced without these specific details. In other instances, well-known features have not been described in detail to avoid unnecessarily complicating the description.

The terminology and phraseology used herein is solely used for descriptive purposes and should not be construed as limiting in scope. Language such as "including," "comprising," "having," "containing," "consisting of," or "involving," and variations thereof, is intended to be broad and encompass the subject matter listed thereafter, equivalents, and additional subject matter not recited.

"Isothermal" as used herein refers to a process that takes place with minimal temperature change. Likewise, "isobaric" as used herein refers to a process that takes place with minimal pressure change. For example, "isothermal sampling," "isobaric sampling," "at line conditions," and variations thereof, as used herein refers to sampling a predominant phase of a multiphase fluid without substantially changing its composition or state.

Figure 1A:
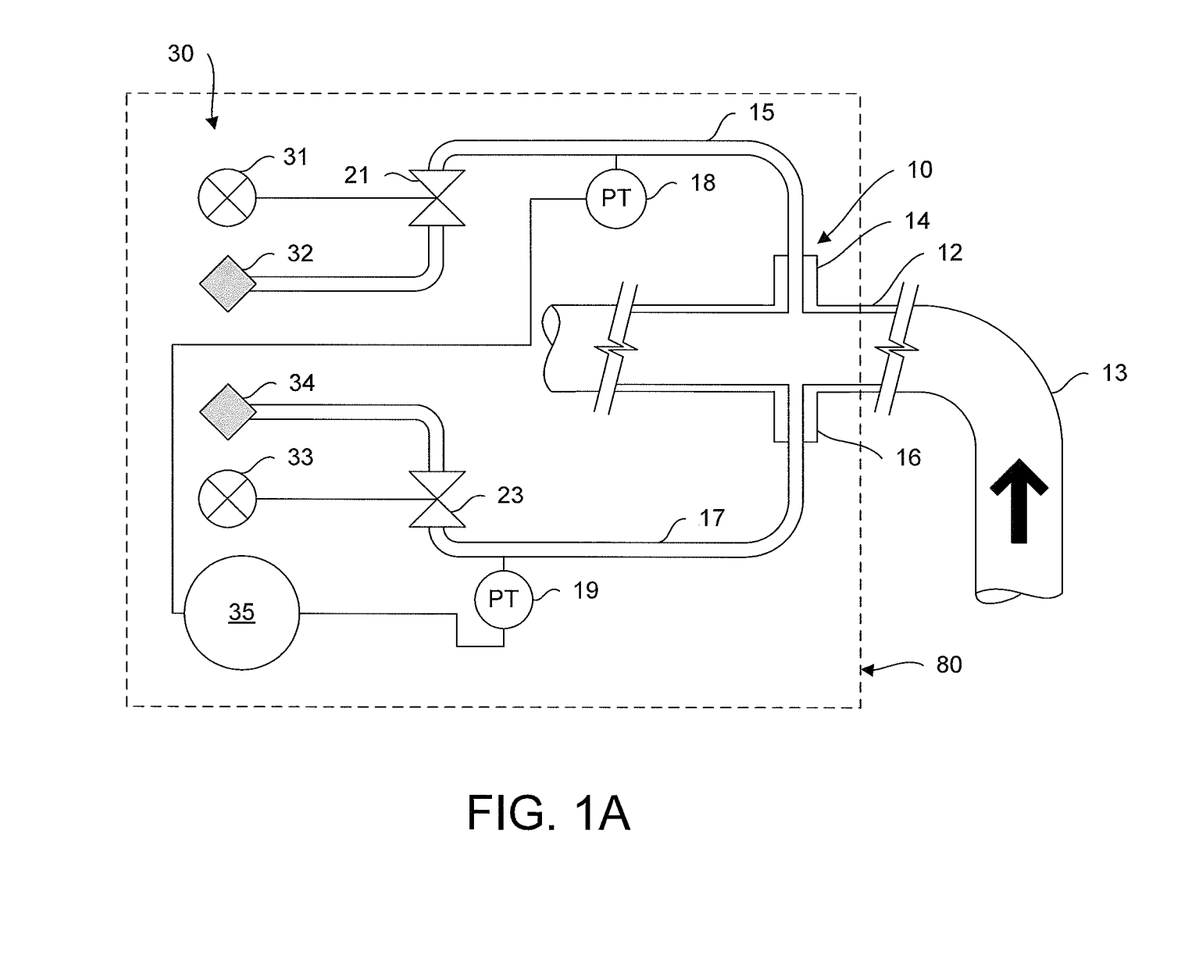
FIG. 1A depicts a schematic overview of a multiphase sampling apparatus attachable to a flowline and attachable to an ROV according to an exemplary embodiment of the present disclosure.

An exemplary embodiment of an isothermal subsea sampling system according to an aspect of the present disclosure is depicted in FIG. 1A. The flowline 12 to which the system may be applied is preferably for use in the oil or gas industry, and is preferably located subsea, either above or below the seabed. It should be understood that subsea includes any depth in any body of water. Access to the flowline 12 is preferably provided by a vehicle sampling apparatus, or a subsea remotely operated vehicle (ROV) skid controlled by an operator on a subsea platform or ship.

In accordance with an exemplary embodiment of the present disclosure, a system and method for collecting the at least one selected phase of a representative sample from a multiphase fluid flowing through the flowline 12 is presented. The removal and analysis of the representative sample, that is, liquid (e.g., oil and water) and gas samples from subsea pipelines and seabed production equipment, may contain multiphase fluid flow across a broad range of fluid types, from gas condensates to heavy oils. The present disclosure allows an operator to collect, store, transport and/or analyze a selected phase sample of the multiphase fluid flowing through the flowline 12 without substantially changing its composition and state. Advantageously, the operator may optimize the well fluid production by testing or analyzing a sample of each selected phase, either independently or in combination, with confidence that the fluid sample substantially simulates line conditions.

The system incorporates a multiphase sampling apparatus 10 (alternatively referred to in this specification as simply "sampling apparatus 10") attachable to the flowline 12 for sampling the representative sample of multiphase fluid flowing through the flowline 12. Additional components of the system, each of which will be explained in more detail hereinafter, include a vehicle sampling apparatus 40, or subsea remotely operated vehicle (ROV); an interface 30 for connecting the sampling apparatus 10 and the vehicle sampling apparatus 40; and a temperature control arrangement 80 for minimizing the temperature difference between the representative sample and the multiphase fluid flowing through the flowline 12.

Figure 3:
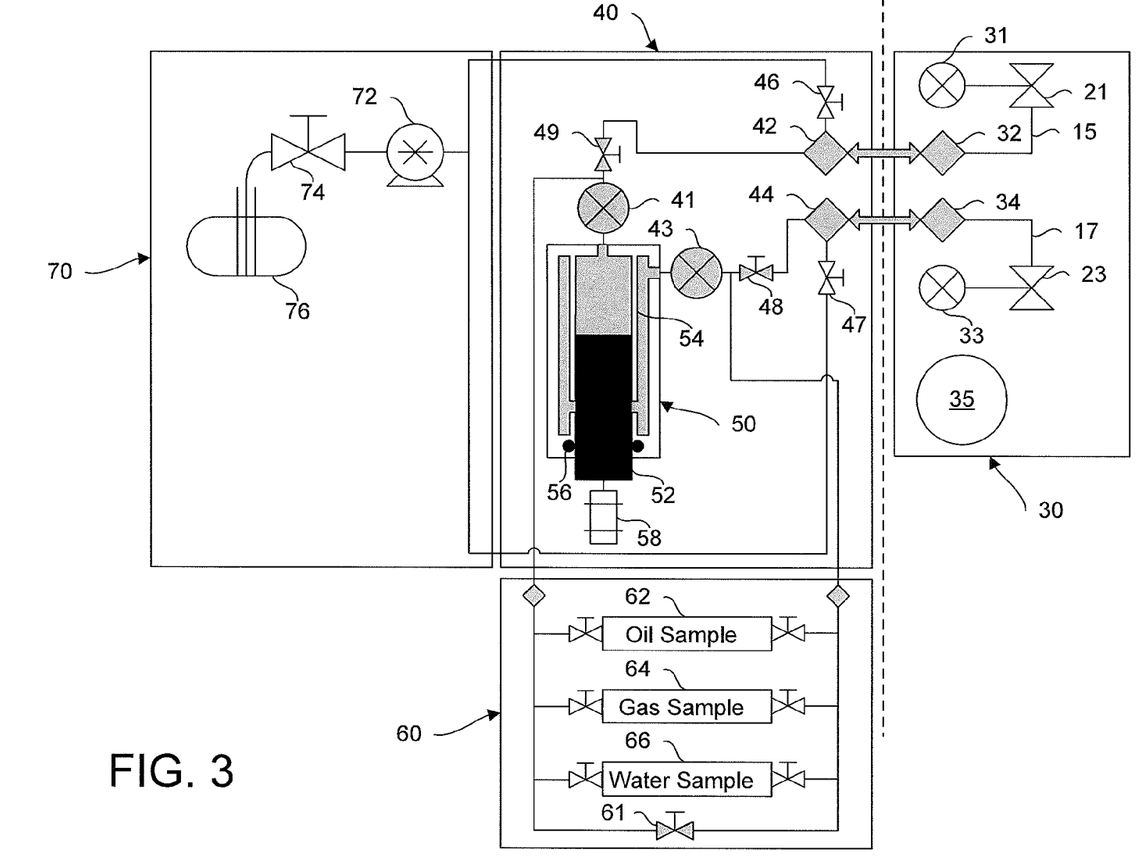
FIG. 3 depicts a schematic overview of a system for collecting a representative sample of multiphase fluid according to an exemplary embodiment of the present disclosure.

Although not shown in FIG. 1A, but implied from the schematics and referenced as 40 in FIG. 3, the vehicle sampling apparatus 40 may also be a diver or a diver operated vehicle. The vehicle sampling apparatus 40 preferably includes a power source, either supplied from the surface or independently generated, and is preferably capable of transporting the fluid sample remotely from the flowline 12. The vehicle sampling apparatus 40 further includes at least one fluid sample collector for storing the selected phase(s) of the representative sample. The vehicle sampling apparatus 40 may include a variety of other features useful for subsea sampling, such as, but not limited to, a plurality of sensors, fluid pumps, hydraulics, extendible arms, a camera, and the like.

In an exemplary embodiment, depicted in FIG. 1A, the sampling apparatus 10 includes a flow conditioner 13, a liquid-rich sampling port 14, and a gas-rich sampling port 16 integrally connected to the flowline 12. The sampling apparatus 10 is configured to extract a selected phase from the multiphase fluid flowing through the flowline 12. The flow conditioner 13 is shown to essentially includes an elbow, or corner, portion of the flowline 12. In this particular embodiment, the flow conditioner 13 is adapted to cause the heavier liquid-rich components to move to the outside surface of the flowline 12, or the superior portion of the flowline 12, due to the centrifugal forces. The lighter gas-rich components will be forced away from the outside of the flowline 12 and be closer to the inside surface of the flowline 12, or the inferior portion of the flowline 12. The liquid-rich sampling port 14 and the gas-rich sampling port 16 are appropriately disposed on the superior portion and inferior portion, respectively, of the flowline 12, positioned downstream, or after, the flow conditioner 13 relative to the direction of multiphase fluid flow.

In an alternative implementation of each embodiment presently disclosed, the sampling apparatus 10 may be positioned on the vehicle sampling apparatus 40, and adapted to attach to any position of the flowline 12 by means of a hydraulic wet connect or the like to collect the representative sample. Moreover, the flow conditioner 13 as referenced herein is not limited to an elbow portion of the flowline 12, and may include a flow conditioner as disclosed in co-pending U.K. Patent Application Nos. 2406386A and 2447908A. That is, the flow conditioner 13 may be based on a combination of orifice plates with different beta ratios set at appropriate axial distances at a location in the flowline 12 upstream from the sampling apparatus 10. Or, the flow conditioner 13 may include a pipe section including: a swirl inducing section; a flow straightener; and an orifice plate. The flow conditioner 13 may have the functionality to keep the flow homogenous (e.g., in terms of liquid-gas velocities) at the sampling cross section. In other words, flow conditioning may be achieved by a variety of techniques, e.g., Venturi, mixing plate, choke and/or the like.

Further depicted in FIG. 1A, a liquid-rich sample line 15 and gas-rich sample line 17 are shown to lead from the liquid-rich sampling port 14 and the gas-rich sampling port 16, respectively, to the interface 30 for selective fluid communication with the vehicle sampling apparatus 40. Control of the liquid-rich sampling port 14 and the gas-rich sampling port 16, and hence the flow of fluid through the liquid-rich sample line 15 and gas-rich sample line 17, is preferably actuated by the vehicle sampling apparatus 40 at the fluid control valves, or ROV-operated control valves 31 and 33, and sample valves 21 and 23. The liquid-rich fluid connection point 32 and gas-rich fluid connection point 34 function to communicate and transfer the fluid from the sampling apparatus 10 to the vehicle sampling apparatus 40, and also function as a barrier to the subsea environment by way of, for example, metal-to-metal dynamic seals. Flow through the liquid-rich sample line 15 and gas-rich sample line 17 may be bi-directional, the operation of which will be explained in more detail hereinafter. It should be noted that while the fluid sample lines 15 and 17 are shown in FIG. 1A as separate and distinct fluid paths, a single path, or a single sample line, leading from a single sample port is contemplated to function in an equivalent manner.

The interface 30, as described above and shown in FIG. 1A, includes ROV-operated control valves 31 and 33, liquid-rich and gas-rich fluid connection points 32 and 34, and a power connection point 35, also referred to in the industry as an electrical wet connect or hot stab. One of the primary functions of the interface 30 is to provide a barrier between the fluid flowing throughout the system and the subsea environment, and a connection between the sampling apparatus 10 and the vehicle sampling apparatus 40 for reliable transfer of fluid and power. Connection between the vehicle sampling apparatus 40 and the interface 30 is preferably a hydrocarbon capable wet connect including a hydraulically actuated stab plate connector, but may include other means of connection known in the industry. Standard valve geometry and subsea actuator technology is preferably used as much as practically possible to allow compatibility with a higher number of ROVs. There may be further electrical connects, namely, a high-power electrical wet stab connect for providing power to the temperature control arrangement 80 and an electrical wet-connect for phase, pressure and temperature sensors 18 and 19, and other measurements. An advantage of these additional connections being available on the interface 30 is that they can provide a means for powerful electrical connections for the use of the system without requiring a permanently positioned high-power source subsea.

The temperature control arrangement 80, schematically depicted in FIG. 1A, is preferably configured to receive power from the vehicle sampling apparatus 40 for minimizing the temperature difference between the selected phase sample and the multiphase fluid flowing through the flowline 12. The temperature control arrangement 80 preferably includes a plurality of heating elements disposed on, in or inside the sample ports 14 and 16, along the length of the sample lines 15 and 17, and/or the connection points 32 and 34. Such heating elements may include, but are not limited to, heating jackets, thermal insulators, a heating device, a temperature regulator, and the like. Each of which may be positioned throughout the system, including the sampling apparatus 10, the vehicle sampling apparatus 40, the sample lines 15 and 17, etc. Preferably, the temperature control arrangement 80 extends between, and includes, the point of sampling at the sampling apparatus 10 to the point of storing the selected phase sample at the fluid sample collector. At certain components and locations of the system, the temperature control arrangement 80 may be passive, taking advantage of the natural heat of the flowline 12 and its contents, or alternatively may be active whereby electrical power is supplied by the vehicle sampling apparatus 40. Another example of an active temperature control arrangement 80 may include heated water provided by the vehicle sampling apparatus 40 to supply energy to the system for maintaining line conditions.

The temperature control arrangement 80 may further include one or more of the temperature sensors 18 and 19 for measuring the temperature of the system. In particular, the temperature sensors 18/19 may be located at or near the liquid-rich sampling port 14 and/or the gas-rich sampling port 16 to measure the temperature of the multiphase fluid flowing through the flowline 12. Additionally, the temperature sensors 18/19 or a plurality of the temperature sensors 18/19 may be located at or near the liquid-rich sample line 15 and/or the gas-rich sample line 17 to measure the temperature of the representative sample. Feedback from the temperature sensors 18 and 19 can be used to maintain the system within a few degrees Celsius, a few tens of degrees Celsius, or a few hundreds of degrees Celsius. The precision of difference between the temperatures of the representative sample and the multiphase fluid flowing through the flowline 12 largely depends on the fluid type and properties (e.g., lean gas or heavy oil).

Figure 1B:
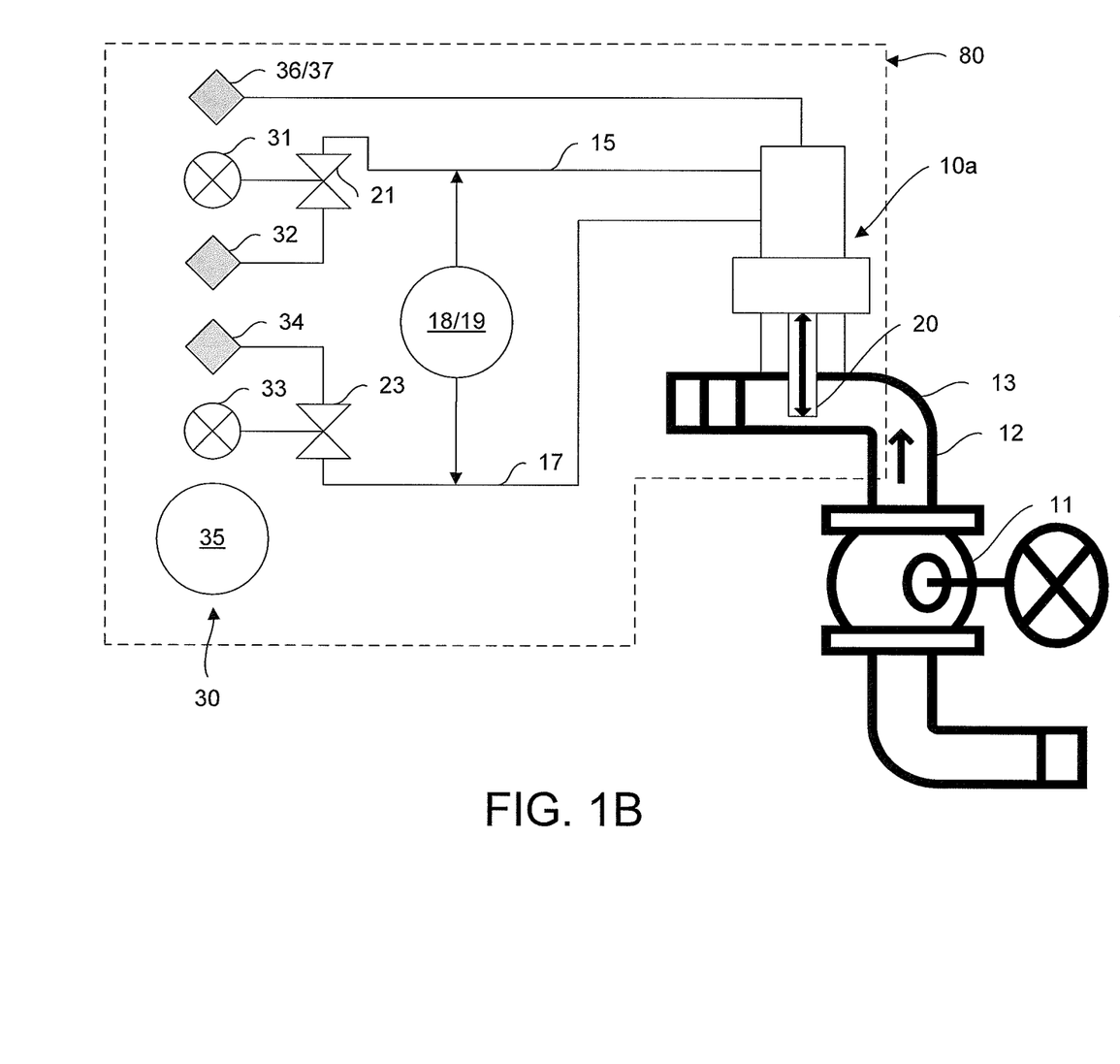
FIG. 1B depicts a schematic overview of a multiphase sampling apparatus attachable to a flowline and attachable to an ROV according to an alternative embodiment of the present disclosure.

In an alternative embodiment, the multiphase sampling apparatus 10a as depicted in FIG. 1B, includes a flow conditioner 13, a flowline valve 11, and a sampling probe 20 for extracting pressure/volume/temperature (PVT) quality samples directly from the flowline 12. The sampling probe 20 can be modified for various apparatus and methods of deployment, embodiments of which will be described in more detail below. In each of these embodiments, isothermal heating and sensors are preferably used to monitor the fluid characteristics of the fluid sampling. The sampling probe 20 is shown to be permanently positioned on the flowline 12 and is depicted at a position on flowline 12 downstream of the flow conditioner 13, or elbow. The sampling probe 20 is positioned downward facing, which is opposite to the typical port for a multiphase sampling device, which is upward facing.

Further depicted in FIG. 1B, the liquid-rich sample line 15 and gas-rich sample line 17 are shown to lead from the sampling probe 20 to the liquid-rich fluid connection point 32 and gas-rich fluid connection point 34 of the interface 30 for selective fluid communication with the vehicle sampling apparatus 40. Control of the fluid flow through the sample lines 15 and 17 may be actuated by the vehicle sampling apparatus 40 via the fluid control valves, or ROV-operated control valves 31 and 33, and sample valves 21 and 23. Moreover, operation of the sampling probe 20 may be actuated by an additional hydraulic connection point(s) 36 and 37 located on the interface 30. In a preferred embodiment, the flowline valve 11 may be ROV-operated to control the flow of multi-phase fluid through the flowline 12, or the flowline valve 11 may operate similar to a blow-out preventer (BOP). The temperature control arrangement 80 for this particular embodiment may additionally include heating elements disposed on, in or inside the sampling probe 20, and a temperature sensor 18/19 at or near the sampling probe 20 to maintain a similar temperature in each phase of the multiphase fluid throughout the system.

Figure 2A:
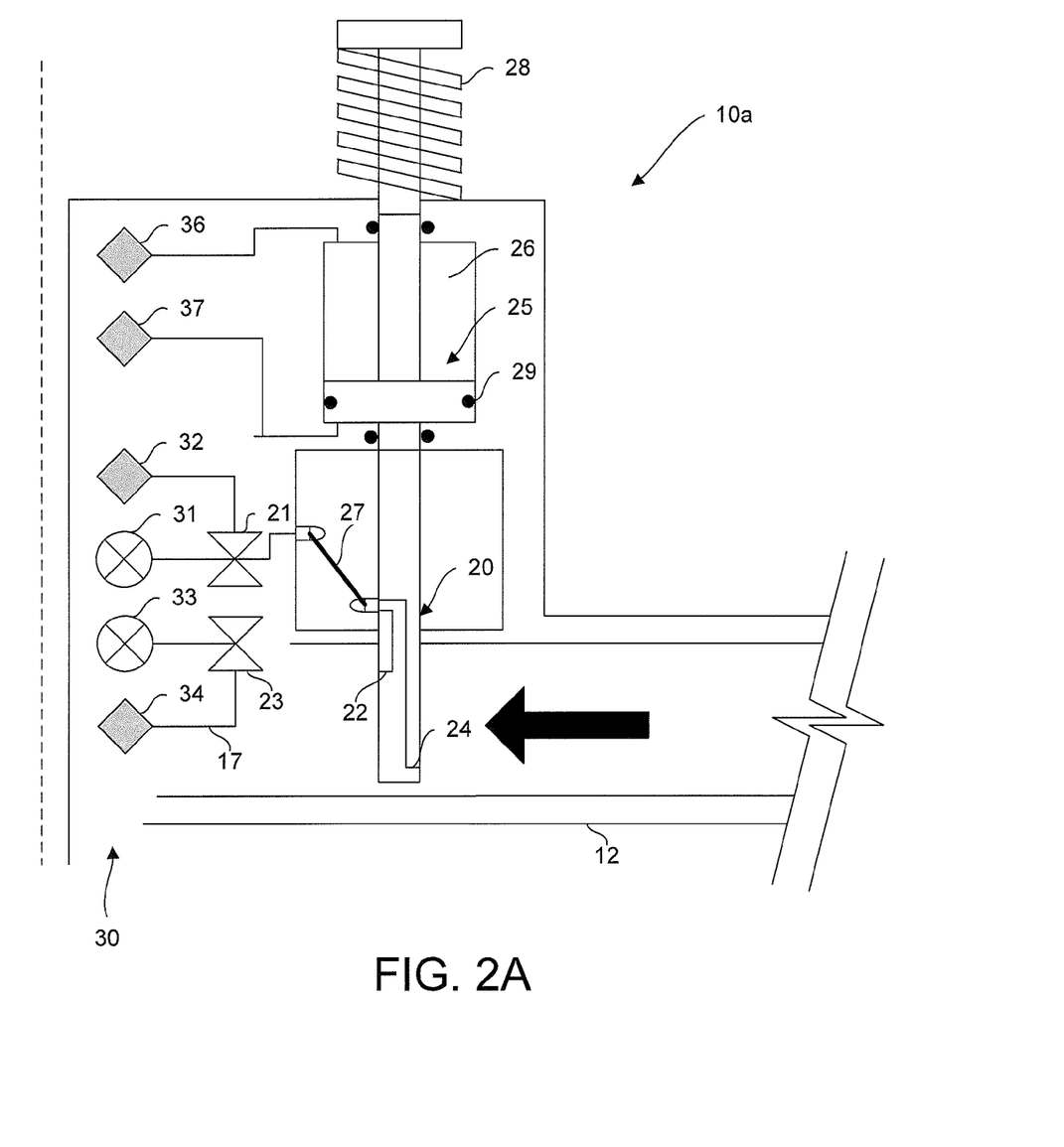
FIG. 2A depicts a schematic overview of a sampling probe inserted into a flowline according to another exemplary embodiment of the present disclosure.
Figure 2B:
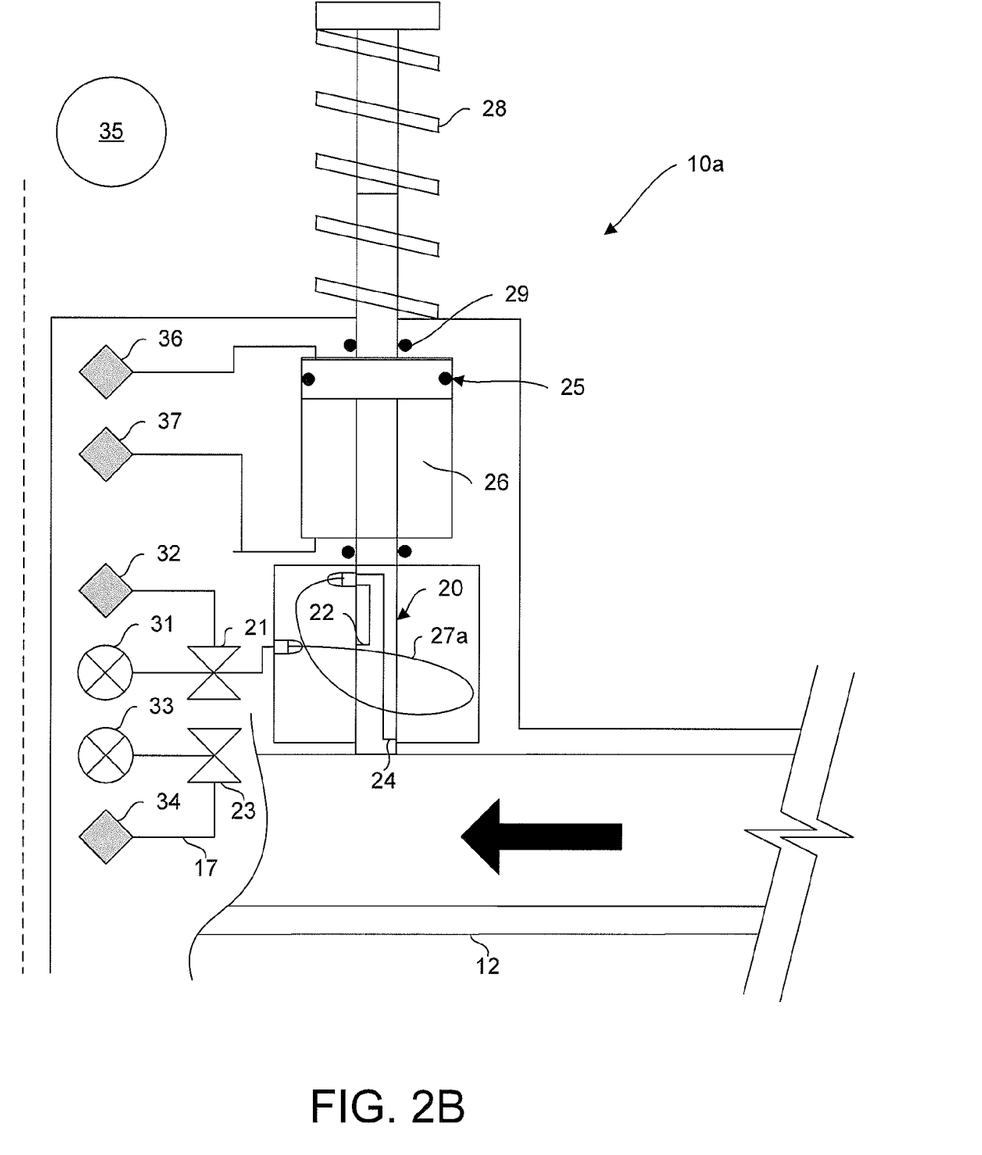
FIG. 2B depicts a schematic overview of a sampling probe retracted from a flowline according to another exemplary embodiment of the present disclosure.

The sampling probe 20 is preferably insertable into and retractable from the flowline 12, as further depicted in FIGS. 2A and 2B. FIG. 2A shows an embodiment of the sampling probe 20 inserted into the flowline 12, whereas FIG. 2B shows another embodiment of the sampling probe 20 retracted from the flowline 12. Where permanently installed sampling probes can erode and block the flowline 12, an insertable and retractable sampling probe 20 can present numerous advantages over such implementations.

The sampling probe 20 preferably includes two ports, a liquid-rich sampling port 22 and a gas-rich sampling port 24, most likely including a metal conduit through the sampling probe 20. The liquid-rich sampling port 22 and the gas-rich sampling port 24 are positioned in accordance with the flow conditioner 13, and may be used as an inlet for a fluid sample, or as an outlet for returning unwanted fluid back into the flowline 12. For example, as is shown in FIG. 2A, the liquid-rich sampling port 22 is positioned at or near the superior portion of the flowline 12 where the heavier liquid-rich components are more likely to displace due to the centrifugal force created by an elbow-like flow conditioner 13; whereas, the gas-rich sampling port 24 is positioned at or near the inferior portion of the flowline 12 where the lighter gas-rich components are likely to be displaced. It should be understood that various configurations of the flow conditioner 13 will lead to a different positioning of the liquid-rich sampling port 22 and the gas-rich sampling port 24 within the flowline 12.

Also shown in FIG. 2A, the liquid-rich sampling port 22 and the gas-rich sampling port 24 are shown to be facing the flow or facing away from the flow in a particular direction. It is also contemplated, that the orientation of the liquid-rich sampling port 22 and the gas-rich sampling port 24 may be in any suitable direction for capturing a predominant phase, such as but not limited to, towards the direction of flow, away from the direction of flow, perpendicular to the direction of flow, and the like. The liquid-rich sampling port 22 and the gas-rich sampling port 24 may further include a sensor(s) for measuring, as an example, flowline pressure and/or flowline temperature, as well as a sensor, such as an optical phase detector, for measuring the desired phase.

Separate alternatives are shown in FIGS. 2A and 2B for communicating the extracted representative sample between the sampling probe 20 and the sample lines 15 and 17 in a method that maintains the representative sample at line conditions and regulates the volume of fluid sampled. In FIG. 2A, a probe sampling line 27 is shown to include a metal tube with knuckles at either end, and a telescopic section in the middle to compensate for length changes during deployment and retraction of the sampling probe 20. Such probe sampling line 27 may utilize elastomers depending on the term of subsea deployment. In FIG. 2B, a probe sampling line 27a is shown to include a small diameter (⅛" for example) flexible line. The ends of which can be welded rather than swaged, and can be fixed into place via metal-to-metal seals. It should be understood that the design and length of the probe sampling line 27 and 27a will be a function of allowable space and probe stroke. The probe sampling lines 27 and 27a may be prepared like a spring to cope with the probe stroke without compromising the mechanical properties of the metal.

In one implementation, the multiphase sampling apparatus 10a is shown to further include a piston 25 integrally connected to sampling probe 20, that can be actuated within a probe actuating chamber 26, a probe spring 28, and a plurality of seals 29 for separating the piston 25 from the flowline 12. The piston 25, and hence the sampling probe 20, may be deployed to a particular position and retracted using any suitable hydraulic actuation means known in the art. The position of sampling probe 20 may be calculated or controlled from the vehicle sampling apparatus 40 with regards to the volume of hydraulic fluid pumped into the probe actuating chamber 26 or by a Linear Variable Differential Transformer (LVDT) or sensor mounted on the hydraulic actuation system. However, it should be understood that deployment of the sampling probe 20, may be actuated by electric motors (not shown) or the like.

An even further embodiment of the system and method according to the present disclosure includes the use of a lubricator type sampling probe deployment (not shown). In this embodiment, the sampling probe 20 is completely removed from the flowline 12 and is fitted to the vehicle sampling apparatus 40. Such embodiment requires a lubricator type system to pressure seal and deploy the sampling probe 20.

The enrichment arrangement and method according to an aspect of the present disclosure includes detecting at least one selected phase of the representative sample and discarding at least one other phase of the representative sample into the flowline 12. The enrichment arrangement may further include separating and storing the selected phase from the unwanted other phase discarded into the flowline 12.

Referring now to FIG. 3, the enrichment arrangement includes at least one phase detector 41 and 43, such as an optical phase detector, preferably a phase detector primarily for measuring the phase boundary and transition between liquid (e.g., oil and/or water) and gas. The enrichment arrangement further includes a fluid pump 50, or an enrichment pump, having a pump cylinder 52, a pump chamber 54, at least one seal 56, and a pump motor 58. The enrichment arrangement further includes a plurality of valves 46, 47, 48 and 49 for controlling the flow of one selected phase or another. The enrichment pump 50, phase detector 41/43, and the combination of valves 48/49 allow the sampling and storage of at least one selected phase of the representative sample at a desired rate in a fluid sample collector 60, which is preferably located on the vehicle sampling apparatus 40. The pump motor 58 may be a ball-screw type that may be operated at a variable rate and direction. For example, any portion of the fluid may be discarded into the flowline 12, preferably at line conditions to minimize pressure drop. Once one of the fluid sample collectors 62, 64, or 66 is full of the selected phase, the representative sample can then be diverted into a different fluid sample collector 62, 64 or 66 for storage, analysis and/or transportation to surface. The enrichment arrangement or vehicle sampling apparatus 40 may further include a sensor for measuring the volume of the selected phase stored in the fluid sample collector 60. For example, by measuring the displacement characteristics of the pump cylinder 52 or by a sensor located within or near the fluid sample collector 60.

The fluid sample collector 60, which may contain multiple sample collectors for each phase (e.g., oil sample collector 62, gas sample collector 64 and water sample collector 66) can be arranged in either a stackable or linear arrangement on the vehicle sampling apparatus 40. Each fluid sample collector 62, 64, and 66 preferably includes electro/mechanical valves for capturing the selected phase of the representative sample and manual valves for bleeding lines and surface removal. Each fluid sample collector 62, 64, and 66 may also include a piston with a seal to allow the selected phase to be maintained at isobaric conditions and allow easy transfer of the fluid sample. The fluid sample collector 60 is preferably adapted to conform to HAZ MAT shipping regulations.

According to another exemplary aspect of the present disclosure, a fluid pump, or plurality of fluid pumps, may be used for returning, or discarding, any portion of the representative sample back into the flowline 12, pressure testing the connection of the vehicle sampling apparatus 40, tuning the flow conditioner 13, maintaining line conditions within the system, unblocking or cleaning the multiphase sampling apparatus 10/10a, the fluid connection points 32/34/42/44, sample lines 15/17, sampling port 14/16/22/24, flow conditioner 13 or fluid flowline 12, and/or deploying the sampling probe 20.

Utilizing the fluid pump or the plurality of fluid pumps described above, a pressure control arrangement 70 is presented to maintain near-isobaric conditions between the representative sample and the multiphase fluid flowing through the flowline 12. The pressure control arrangement 70 preferably includes at least one fluid pump 72 in selective fluid communication with at least one of the fluid connection points 42, 44, 32, and/or 34 between the multiphase sampling apparatus 10/10a and the vehicle sampling apparatus 40. The pressure control arrangement 70 may also include a plurality of control valves, such as valves 74, 46 and 47, a pressurized pump reservoir 76, and at least one pressure sensor 18 and 19 for measuring the pressure of the system. The control valves 46 and 47 are adapted to pressure test each hot stab individually before allowing fluid flow. The pressurized pump reservoir 76 and control valve 74 are adapted to initially provide a significant amount of pressure (e.g., greater than the flowline pressure) to pressure test the fluid connections 42, 44, 32, and 34, as well as unblock or clean the fluid flow lines throughout the system.

In an even further aspect of the present disclosure, the system may include analysis means locatable on the vehicle sampling apparatus 40 for analyzing the representative sample near the flowline 12. Advantageously, subsea analysis allows the operator to determine if transportation of the representative sample to the surface is necessary. The analysis means can typically include any suitable known equipment which makes use of varied forms of known oilfield fluid analysis technologies. Such analysis means may include, but are not limited to, wireline technologies, such as a modular dynamic formation tester, an optical fluid analyzer, low shock sampling, PVT analysis, and sensors for measuring the nuclear attenuation of a gamma ray source one phase at a time, for example, by way of gamma ray attenuation performed at line conditions, or the like.

In operation, a preferred method for collecting at least one selected phase of a representative sample from a multiphase fluid flowing through the flowline 12 located subsea includes connecting the vehicle sampling apparatus 40 to the interface 30 located proximate the multiphase sampling apparatus 10/10a; measuring a pressure and temperature of the multiphase fluid flowing through the flowline 12; activating the temperature control arrangement 80 and the pressure control arrangement 70 to simulate conditions similar to the measured temperature and pressure of the multiphase fluid flowing through the flowline 12; selectively sampling the at least one selected phase of the representative sample from the multiphase fluid; and storing the at least one selected phase of the representative sample in the fluid sample collector 60 at conditions similar to the measured temperature and pressure of the multiphase fluid flowing through the flowline 12.

Figure 4A:
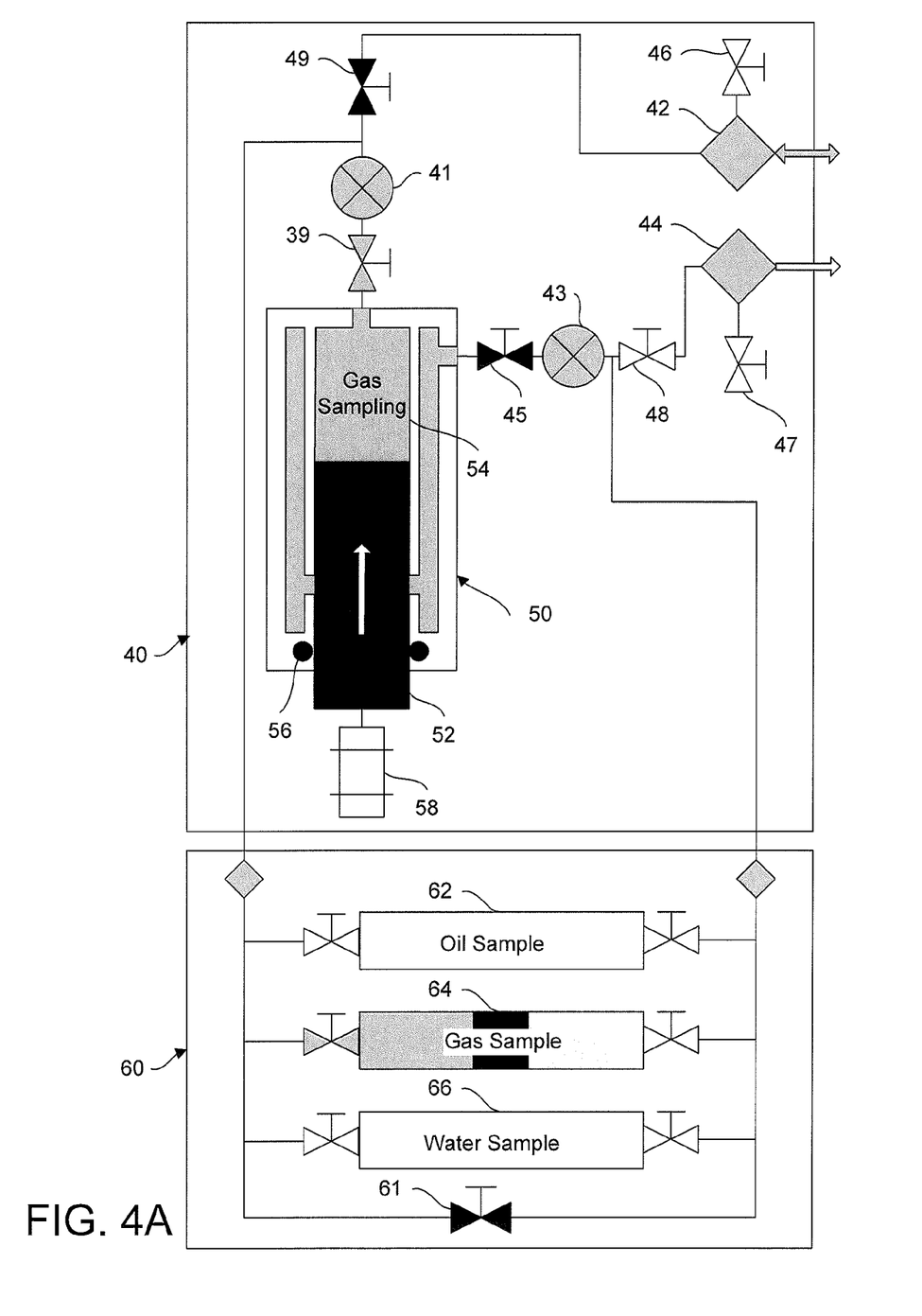
FIG. 4A depicts a schematic illustration of a method for collecting a representative gas sample according to an exemplary embodiment of the present disclosure.

Referring now to FIG. 4A, there is illustrated an example for sampling a representative gas sample. After the vehicle sampling apparatus 40 has connected to the multiphase sampling apparatus 10/10a, and the temperature and pressure of the system is determined to be at or near line conditions, the representative gas sample may be drawn into the pump chamber 54 of the enrichment pump 50. The valves surrounding the gas sample collector 64 are opened, and the control valves 49, 45 and 61 are closed. The enrichment pump 50, pumps the gas out of the pump chamber 54 into the gas sample collector 64. Depending on the volume of the enrichment pump 50 and the gas sample collector 64 it may take a number of cycles to fill the gas sample collector 64. In one implementation of the present embodiment, the gas sample collector 64 may contain a hydraulic fluid, such as water-glycol, which can be displaced by the representative gas sample and vented back into the flowline 12. The pressure of the system should be maintained at isobaric conditions with the exception of the hydraulics and seal friction.

Figure 4B:
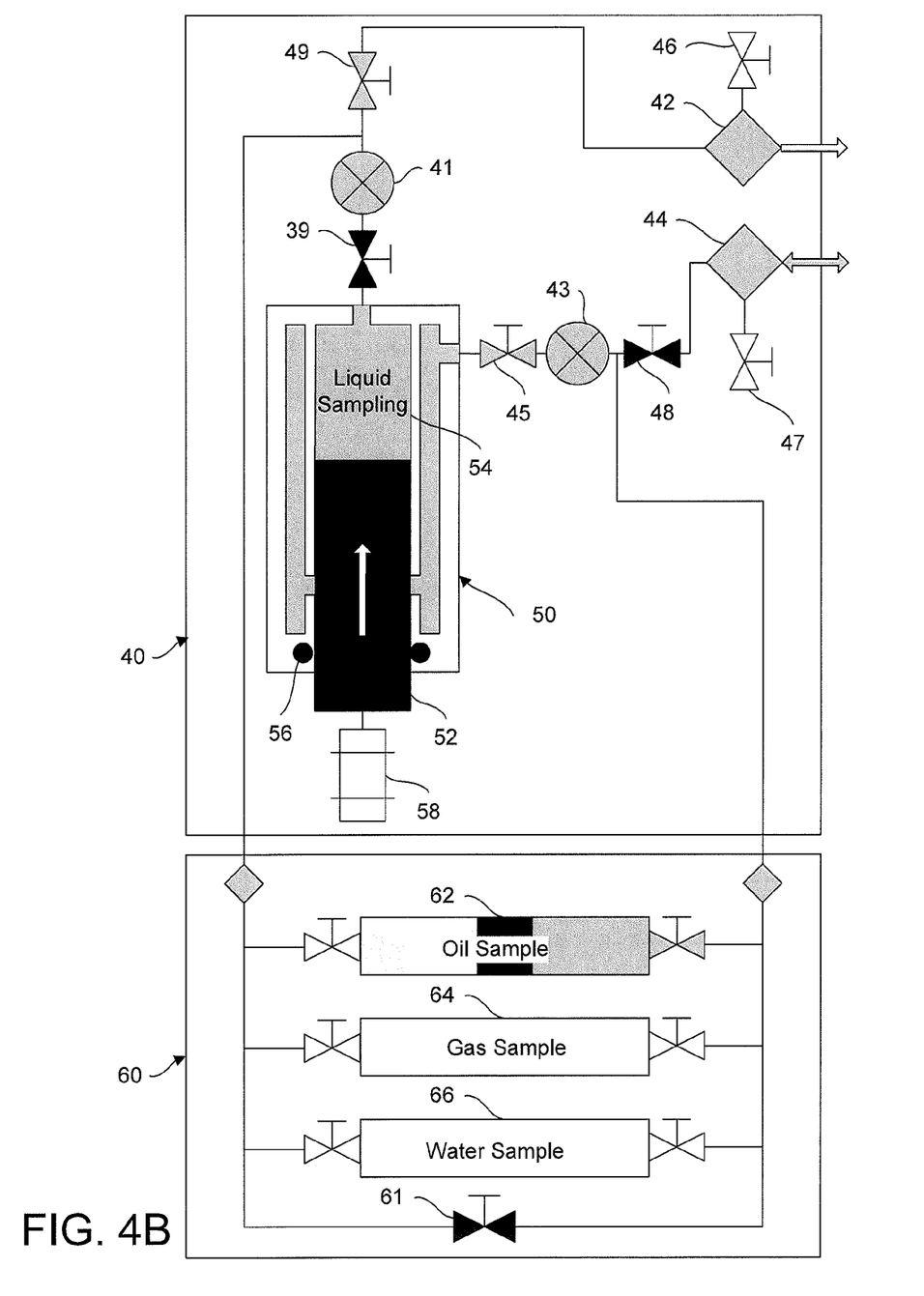
FIG. 4B depicts a schematic illustration of a method for collecting a representative oil sample according to an exemplary embodiment of the present disclosure.

Referring now to FIG. 4B, there is illustrated an example for sampling a representative liquid sample. After the vehicle sampling apparatus 40 has connected to the multiphase sampling apparatus 10/10a, and the temperature and pressure of the system is determined to be at or near line conditions, the representative liquid sample may be drawn into the pump chamber 54 of the enrichment pump 50. The valves surrounding the liquid sample collector 62 are opened, and the control valves 39, 48 and 61 are closed. The enrichment pump 50, pumps the liquid out of the pump chamber 54 into the liquid sample collector 62. Depending on the volume of the enrichment pump 50 and the liquid sample collector 62 it may take a number of cycles to fill the liquid sample collector 62. In one implementation of the present embodiment, the liquid sample collector 62 may contain a hydraulic fluid, such as water-glycol, which can be displaced by the representative liquid sample and vented back into the flowline 12. The pressure of the system should be maintained at isobaric conditions with the exception of the hydraulics and seal friction. Water sampling can be performed in a similar manner via suitable activation of the water sample collector 62 and the corresponding valves.

Although the present disclosure has been described with reference to exemplary embodiments and implementations thereof, the present disclosure is not to be limited by or to such exemplary embodiments and/or implementations. Rather, the systems and methods of the present disclosure are susceptible to various modifications, variations and/or enhancements without departing from the spirit or scope of the present disclosure. Accordingly, the present disclosure expressly encompasses all such modifications, variations and enhancements within its scope.

What is claimed is:

1. A system for collecting at least one selected phase of a representative sample from a multiphase fluid flowing through a flowline, the system comprising:
   a multiphase sampling apparatus attachable to a flowline for sampling a representative sample of a multiphase fluid flowing through the flowline, wherein the multiphase sampling apparatus comprises a first sampling port and a second sampling port in fluid communication with the multiphase fluid flowing through the flowline for sampling the representative sample;
   a vehicle sampling apparatus locatable proximate the flowline, the vehicle sampling apparatus comprising a power supply and a fluid sample collector for storing the at least one selected phase of the representative sample;
   an interface for connecting the multiphase sampling apparatus and the vehicle sampling apparatus; and
   a heating element configured to minimize the temperature difference between the representative sample and the multiphase fluid flowing through the flowline.

2. The system of claim 1, which is locatable subsea.

3. The system of claim 2, wherein the vehicle sampling apparatus is a subsea remotely operated vehicle (ROV).

4. The system of claim 3, wherein the vehicle sampling apparatus is operable to transport the at least one selected phase of the representative sample remote from the flowline.

5. The system of claim 1, further comprising an enrichment arrangement in fluid communication with the fluid sample collector, the enrichment arrangement configured to detect the at least one selected phase of the representative sample, and discard at least one other phase of the representative sample into the flowline.

6. The system of claim 5, wherein the enrichment arrangement is locatable at one or more of the vehicle sampling apparatus, the multiphase sampling apparatus, the flowline, or the interface.

7. The system of claim 5, wherein the enrichment arrangement further includes a phase separator for separating the phases of the representative sample of the multiphase fluid.

8. The system of claim 1, further comprising a pressure control arrangement having at least one fluid pump in selective fluid communication with at least one fluid communication point between the multiphase sampling apparatus and the vehicle sampling apparatus, wherein the at least one fluid pump is capable of minimizing the pressure difference between the representative sample and the multiphase fluid flowing through the flowline.

9. The system of claim 8, further comprising at least one pressure sensor for measuring the pressure of the multiphase fluid flowing through the flowline and at least one other pressure sensor for measuring the pressure of the representative sample.

10. The system of claim 1, wherein the first sampling port and the second sampling port are in selective fluid communication with the multiphase fluid flowing through flowline for sampling the representative sample.

11. The system of claim 10, further comprising a flow conditioner positioned upstream of the first sampling port and the second sampling port relative to the direction of multiphase fluid flowing through the flowline.

12. The system of claim 11, wherein the flow conditioner includes an elbow portion of the flowline.

13. The system of claim 1, wherein the multiphase sampling apparatus comprises a sampling probe capable of insertion into the flowline for sampling the representative sample of the multiphase fluid flowing through the flowline.

14. The system of claim 13, wherein the sampling probe is insertable into the flowline by an extension mechanism, when a sample is to be collected.

15. The system of claim 13, wherein the sampling probe is retractable from the flowline by an extension mechanism, when the sampling probe is not to be used for sampling.

16. The system of claim 13, wherein the sampling probe includes at least one fluid analysis sensor.

17. The system of claim 13, wherein the first sampling port and the second sampling port are disposed on the sampling probe, and wherein the first sampling port is positioned near a superior portion of the flowline, and the second sampling port is positioned near an inferior portion of the flowline.

18. The system of claim 1, wherein the multiphase sampling apparatus is permanently positioned on the flowline.

19. The system of claim 1, wherein the multiphase sampling apparatus is locatable on the vehicle sampling apparatus.

20. The system of claim 1, further comprising a fluid analysis sensor locatable on the vehicle sampling apparatus that analyzes the collected fluid sample.

21. The system of claim 1, further comprising at least one fluid pump in fluid communication with the multiphase sampling apparatus, wherein the at least one fluid pump is capable of cleaning the multiphase sampling apparatus sample lines.

22. The system of claim 1, further comprising a plurality of heating elements disposed upon a plurality of sample lines leading away from the multiphase sampling apparatus.

23. The system of claim 22, further comprising at least one temperature sensor for measuring the temperature of the multiphase fluid flowing through the flowline, and at least one other temperature sensor for measuring the temperature of the representative sample.

24. The system of claim 1, wherein the interface comprises at least one fluid control valve operable by the vehicle sampling apparatus, a first connection point and a second connection point for selectively transferring the at least one selected phase of the representative sample between the multiphase sampling apparatus and the vehicle sampling apparatus.

25. The system of claim 1, wherein the interface comprises at least one power connection point for transferring power to the heating element.

26. The system of claim 1, wherein the interface comprises at least one hydraulic connection point for actuating the multiphase sampling apparatus.

27. The system of claim 1, wherein the first sampling port is located in a liquid-rich location in the flowline, and
wherein the second sampling port is located in a gas-rich location in the flowline.

28. A method for collecting at least one selected phase of a representative fluid sample from a multiphase fluid flowing through a flowline located subsea, the method comprising:
connecting a vehicle sampling apparatus having a fluid sample collector to an interface located proximate a multiphase sampling apparatus, wherein the multiphase sampling apparatus is attachable to the flowline and includes a first sampling port and a second sampling port in fluid communication with the multi base fluid flowing through the flowline;
measuring a pressure and temperature of the multiphase fluid flowing through the flowline;
maintaining the temperature and pressure of the multiphase fluid flowing through the vehicle sampling apparatus substantially the same as the temperature and pressure, respectively, of the multiphase fluid flowing through the flowline;
selectively sampling the at least one selected phase of a representative sample from the multiphase fluid flowing through the flowline through at least one of the first sampling port and the second sampling port; and
storing the at least one selected phase of the representative sample in the fluid sample collector.

29. The method of claim 28, further comprising enriching the at least one selected phase of the representative sample, wherein enriching comprises the steps of:
detecting the at least one selected phase of the representative sample; and
discarding at least one other phase of the representative sample into the flowline.

30. The method of claim 29, further comprising separating the at least one selected phase of the representative sample from the at least one other phase of the representative sample with a flow conditioner positioned upstream of the first sampling port and the second sampling port relative to the direction of multiphase fluid flowing through the flowline.

31. The method of claim 28, further comprising disconnecting the vehicle sampling apparatus from the interface.

32. The method of claim 31, further comprising transporting the at least one selected phase of the representative sample stored in the fluid sample collector to a position remote from the flowline.

33. The method of claim 28, further comprising analyzing a plurality of fluid characteristics of the at least one selected phase of the representative sample.

34. The method of claim 28, further comprising cleaning the multiphase sampling apparatus by means of a fluid pump.

35. The method of claim 28, wherein sampling comprises inserting a sampling probe into the flowline by an extension mechanism.

36. The method of claim 35, further comprising retracting a sampling probe from the flowline by an extension mechanism.

37. The method of claim 28, further comprising pressure testing the multiphase sampling apparatus by means of a fluid pump locatable on the vehicle sampling apparatus.

38. The method of claim 28 further comprising:
placing the first sampling port in a liquid-rich location in the flowline; and
placing the second sampling portion in a gas-rich location in the flowline.

39. A system for collecting at least one selected phase of a representative sample from a multiphase fluid flowing through a flowline, the system comprising:
a multiphase sampling apparatus attachable to a flowline for sampling a representative sample of a multiphase fluid flowing through the flowline;
a vehicle sampling apparatus configured to be coupled to the multiphase sampling apparatus, the vehicle sampling apparatus comprising a fluid sample collector for storing the at least one selected phase of the representative sample;
an interface for coupling the multiphase sampling apparatus and the vehicle sampling apparatus, wherein the interface includes a liquid-rich fluid connection point and a gas-rich fluid connection point for selectively transferring the at least one selected phase of the representative sample between the multiphase sampling apparatus and the vehicle sampling apparatus; and
a heating element configured to minimize the temperature difference between the representative sample and the multiphase fluid flowing through the flowline.

40. The system of claim 39, wherein the vehicle sampling apparatus further comprises a power supply; wherein the heating element configured to receive power from the power supply on the vehicle sampling apparatus.

41. The system of claim 40, wherein the multiphase sampling apparatus comprises a liquid-rich sampling port and a gas-rich sampling port in selective fluid communication with the multiphase fluid flowing through flowline for sampling the representative sample.

42. The system of claim 41, wherein the system further comprises a flow conditioner positioned upstream of the liquid-rich sampling port and gas-rich sampling port relative to the direction of multiphase fluid flowing through the flowline.

43. The system of claim 42, wherein the flow conditioner includes an elbow portion of the flowline.

* * * * *